(12) United States Patent
Böttcher et al.

(10) Patent No.: US 7,618,988 B2
(45) Date of Patent: Nov. 17, 2009

(54) USE OF SUBSTITUTED AMINOMETHYL CHROMANS

(75) Inventors: Henning Böttcher, Darmstadt (DE); Ralf Devant, Darmstadt (DE); Maria Devant, legal representative, Darmstadt (DE); Gerd Bartoszyk, Weiterstadt (DE); Hermann Russ, Frankfurt am Main (DE); Frank Weber, Dietzenbach/Steinberg (DE); Christoph Seyfried, Seeheim-Jugenheim (DE)

(73) Assignee: Merck Patentgesellschaft, Darmstadt (DE)

( * ) Notice: Subject to any disclaimer, the term of this patent is extended or adjusted under 35 U.S.C. 154(b) by 361 days.

(21) Appl. No.: 10/489,960

(22) PCT Filed: Aug. 12, 2002

(86) PCT No.: PCT/EP02/09001

§ 371 (c)(1),
(2), (4) Date: Nov. 21, 2005

(87) PCT Pub. No.: WO03/024960

PCT Pub. Date: Mar. 27, 2003

(65) Prior Publication Data

US 2006/0229339 A1 Oct. 12, 2006

(30) Foreign Application Priority Data

Sep. 19, 2001 (EP) ................... 01122377

(51) Int. Cl.
| | | |
|---|---|---|
| A61K 31/135 | (2006.01) | |
| A61K 31/33 | (2006.01) | |
| A61K 31/395 | (2006.01) | |
| A61K 31/535 | (2006.01) | |
| A61K 31/54 | (2006.01) | |
| A61K 31/58 | (2006.01) | |

(52) U.S. Cl. ................. 514/337; 514/222.2; 514/277; 514/332; 514/336; 514/279; 514/449; 514/456; 514/646; 514/727; 514/751; 514/753; 514/759

(58) Field of Classification Search ............ 514/337, 514/183, 222.2, 277, 332, 336, 279, 449, 514/646, 727, 741, 751, 753, 759, 456
See application file for complete search history.

(56) References Cited

U.S. PATENT DOCUMENTS

| 5,756,521 A | 5/1998 | Mewshaw |
| 5,767,132 A | 6/1998 | Bottcher et al. |

OTHER PUBLICATIONS

N. Hewitt, et al., "Studies Comparing in vivo . . . Hepatocyte Cultures", *Drug Metabolism and Disposition*, (2001), 29(7), 1042-1050.
R.E. Mewshaw, et al., "New Generation Dopaminergic . . . D2 Template", *Bioorganic & Medicinal Chemistry Letters*, vol. 12, pp. 271-274 (2002).
A. Kuehler, et al., "Dyskinesien Bei. . . Parkinson Syndrome", *Nervenheilkunde*, Schattauer, Stuttgart, vol. 19, No. 9, pp. 482-488 (2000).
S.L. Shefrin, et al., "Therapeutic Advances in Idiopathic Parkinsonism", *Expert Opinion on Investigational Drugs*, vol. 8, No. 10, pp. 1565-1588 (Oct. 1999).

*Primary Examiner*—Sreeni Padmanabhan
*Assistant Examiner*—Sahar Javanmard
(74) *Attorney, Agent, or Firm*—Millen, White, Zelano, Branigan, P.C.

(57) ABSTRACT

Compounds of formula I in which R has a meaning as indicated in claim 1, or one of their optical isomers or pharmaceutically acceptable salts, used for the treatment of extrapyramidal movement disorders and/or adverse effects in extrapyramidal movement disorders and/or for the treatment of extrapyramidal symptoms (EPS) induced by neuroleptics.

(I)

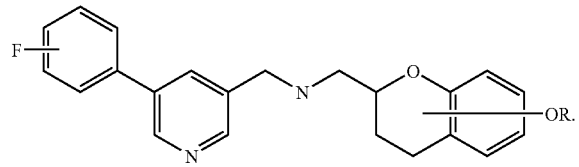

20 Claims, No Drawings

USE OF SUBSTITUTED AMINOMETHYL CHROMANS

The present invention relates to the novel use of substituted aminomethyl chromans for the treatment of movement disorders and of adverse effects induced by drugs administered to treat extrapyramidal movement disorders.

The invention preferably relates to the use of substituted aminomethyl chromans of formula I

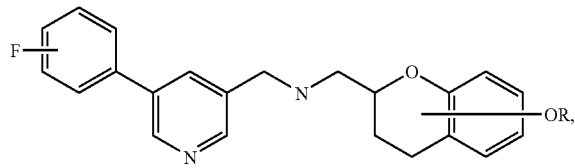

I in which
R represents hydrogen or a hydroxyl protecting group,
and their optical isomers and pharmaceutically acceptable salts or solvates, in particular 2-({[5-(4-fluorophenyl)-pyridin-3ylmethyl]-amino}-methyl)-chroman-4-ol, 2-({[5-(4-fluorophenyl)-pyridin-3ylmethyl]-amino}-methyl)-chroman-7-ol, 2-({[5-(4-fluorophenyl)-pyridin-3ylmethyl]-amino}-methyl)-chroman-8-ol or an optical isomer or physiologically acceptable salts or solvates thereof, for the manufacture of a medicament for the treatment of extrapyramidal movement disorders and/or for the manufacture of a medicament for the treatment of adverse effects of anti-Parkinsonian drugs in extrapyramidal movement disorders and/or for the manufacture of a medicament for the treatment of extrapyramidal symptoms (EPS) induced by neuroleptics. The compounds of Formula I are especially useful in the treatment of dyskinesia.

U.S. Pat. No. 5,767,132 describe similar aminomethyl chroman derivatives which are suitable for prophylaxis and control of the sequelae of cerebral infarction (apoplexia cerebri) such as stroke and cerebral ischaemia, for prophylaxis and control of cerebral disorders, e.g. migraine, especially in geriatrics in a manner similar to certain ergot alkaloids, the treatment of anxiety, tension and depression states, sexual dysfunctions caused by the central nervous system, for disturbances in sleep or absorption of food or for the treatment of psychosis (schizophrenia).

Additionally, they are suitable to eliminate cognitive deficiencies, to improve powers of learning and memory and to treat Alzheimer's disease. They can be furthermore used for treating side-effects in the treatment of hypertension, in endocrinology and gynecology, e.g. for the treatment of acromegaly, hypogonadism, secondary amenorrhea, premenstrual syndrome or undesired puerperal lactation.

Similar compounds are described in Drug Metabolism and Disposition, Vol. 29, No. 7, 1042-1050, 2001.

In contrast to the compounds disclosed in U.S. Pat. No. 5,767,132, the compounds according to formula I are merely agonists of the 5-$HT_{1A}$ receptor and antagonists of the dopamine D4 receptor. They do not show inhibitory effects on the dopamine D2 or D3 receptor.

The unexpected advantage of the compounds of formula I and particularly with R=H and F in 4-position of the phenyl ring, i.e. is indeed their lack of any antagonstic effects on dopamine D2 (and D3) receptors. In strong contrast to the D4 receptor, antagonistic properties at the dopamine D2 receptor and—even if less pronounced D3 receptors—are associated with the induction of various extrapyramidal motor disturbances which are to be treated with the compounds of formula I.

The principle of the preparation of the aminomethyl chromans of formula I to be used according to the invention is disclosed in U.S. Pat. No. 5,767,132. U.S. Pat. No. 5,767,132 is herein incorporated by reference.

Analoguosly to the method described in U.S. Pat. No. 5,767,132, compounds of formula I according to claim 1 and their optical isomers and/or their pharmaceutical acceptable salts and solvates can be prepared e.g. in that (a) a compound of formula II

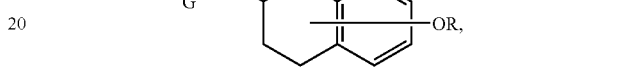

II in which G is Cl, Br, I, alkylsulfonyloxy having 1 to 6 C-atoms or arylsulfonyloxy having 6 to 10 C-atoms and R is a hydroxy protecting group is reacted with an amine of formula III

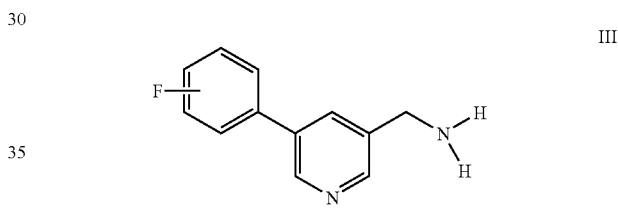

III and, optionally, cleaving the hydroxy protecting group to obtain compounds of formula I, in which R=H;

or (b) a compound of formula IV, prepared as described in U.S. Pat. No. 5,767,132

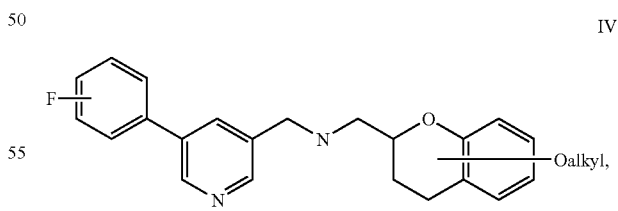

IV in which alkyl is an alkyl group having 1 to 4 C atoms, is dealkylated with a dealkylating agent to obtain compounds of formula I, in which R=H.

Especially preferred is a method (c) to obtain compounds of formula IA

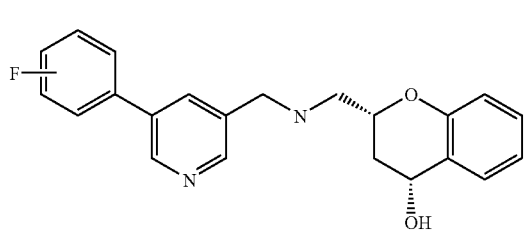

IA having a defined stereochemistry, wherein a chromaneamine of the formula V

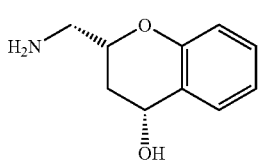

V is reacted with an aldehyde of formula VI

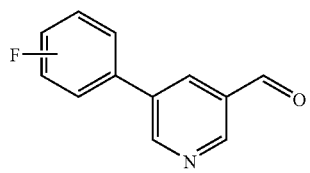

VI and treated a hydride donor, preferably a complex hydride, such as sodium borohydride.

The novel compounds of formula IA are also an object of the present invention.

The starting compound of formula V for Method (c) is preferably obtained by use of a compound of formula VII (obtainable by enantioselective catalytic hydrogenation and crystallization according to WO 02/20507)

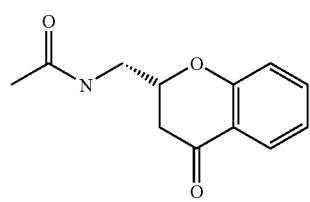

VII which is hydrogenated to yield after optional crystallization an enanatiomerically and diastereomerically pure compound of formula VII.

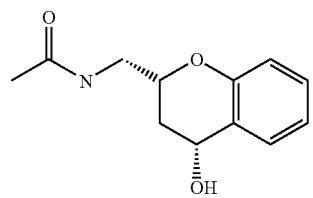

VIII

The compound of formula VIII is hydrolysed to the compound of formula V by standard methods, preferably by treatment with a solution of alkali hydroxide, such as sodium hydroxide.

Surprisingly, in a preferred method for the manufacture of the compound of formula VIII, the compound of formula VII

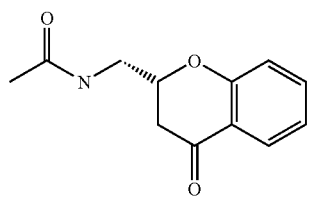

VII is diastereoselectively hydrogenated by a complex hydride, preferably alkali borohydride such as sodium borohydride in an alcohol, such as methanol or ethanol, thus leading after optional crystallization an enanatiomerically and diastereomerically pure compound of formula VIII.

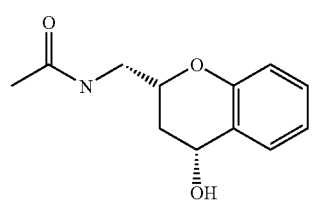

VIII

This way of hydrogenation of the compound of formula VII has the advantage of providing the compound VIII with no or only minor amounts of undesired diastereomer VIIIa:

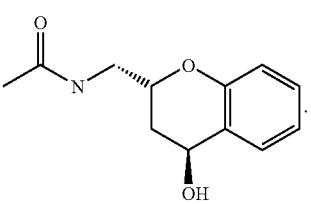

VIIIa

Therefore, the present invention also relates to a process for the preparation of compounds of formula IA

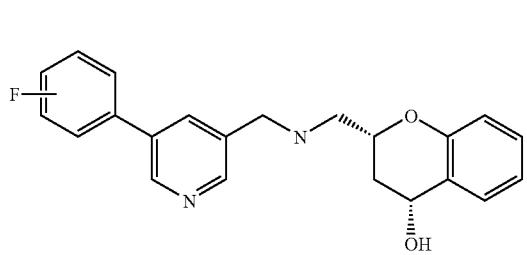

IA having a defined stereochemistry, wherein a chromaneamine of the formula V

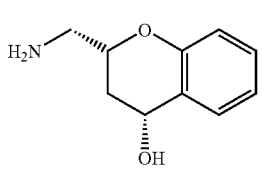

V is reacted with an aldehyde of formula VI

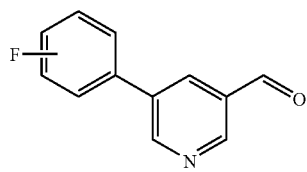

VI and treated a hydride donor.

The invention also relates to a process for the preparation of compounds of formula IB comprising the following steps:

a) hydrogenation of a compound of formula VII

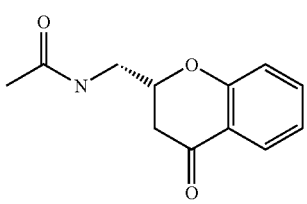

VII to a compound VIII,

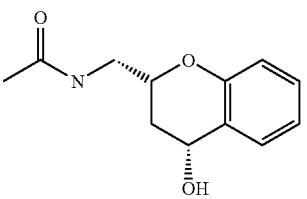

VIII which is and optionally crystallized for purification, b) hydrolysation of the compound VIII obtained in step a) to a compound of formula V

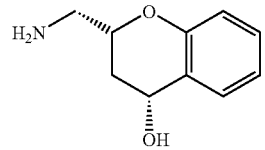

V c) reaction of a compound of formula V obtained in step b) with a compound of formula VI and treatment with a hydride donor

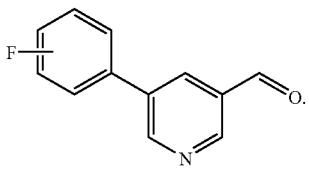

VI

Preferred is the above method for the preparation of Formula IA, wherein the hydrogenation of a compound of formula VII to a compound VIII in step a), is performed diastereoselectively by a complex hydride, preferably alkali borohydride such as sodium borohydride in an alcohol, such as methanol or ethanol.

Especially preferred is the above procedure to prepare (2R,4R)-2-({[5-(4-fluorophenyl)-pyridin-3ylmethyl]-amino}-methyl)-chroman-4-ol by using a compound of formula VIA instead of VI

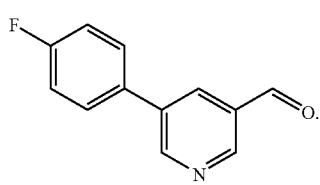

VIA

The alkyl group in formula IV is preferably unbranched and has 1, 2, 3, or 4 C atoms, and is preferably methyl, ethyl, propyl, isopropyl, butyl, isobutyl, sec-butyl or tert-butyl. Particularly preferred is methyl.

In alkylsulfonyloxy having 1 to 6 C-atoms, the alkyl moiety can be methyl, ethyl, propyl, isopropyl, butyl, pentyl or hexyl. Particularly preferred for alkylsulfonyloxy is methanesulfonyloxy.

In arylsulfonyloxy having 6 to 10 C-atoms, the aryl moiety can be phenyl, o-, m-, or p- tolyl, o-, m-, or p-ethylphenyl, o-, m-, or p-propylphenyl or naphthyl. Particularly preferred for arylsulfonyloxy is benzenesulfonyloxy, p-toluenesulfonyloxy, naphthalene-1- or naphthalene-2-sulfonyloxy.

The expression "hydroxyl protective group" is also generally known and relates to groups which are suitable for protecting a hydroxyl group against chemical reactions, but which are easily removable after the desired chemical reaction has been carried out at other positions in the molecule.

Typical groups of this type are unsubstituted or substituted aryl, aralkyl, aroyl or acyl groups, furthermore also alkyl-groups, alkyl-, aryl- or aralkylsilylgroups or O,O— or O,S-acetals. The nature and size of the hydroxyl protective groups is not critical, since they are removed again after the desired chemical reaction or reaction sequence; groups having 1-20, in particular 1-10 C atoms, are preferred. Examples of hydroxyl protective groups are, inter alia, benzyl, 4-methoxybenzyl or 2,4-dimethoxybenzyl, aroyl groups such as benzoyl or p-nitrobenzoyl, acyl groups such as acetyl or pivaloyl, p-toluolsulfonyl, alkyl groups such as methyl or tert-butyl, but also allyl, alkylsilyl groups such as trimethylsilyl (TMS), triisopropylsilyl (TIPS), tert-butyldimethylsilyl (TBS) or triethylsilyl, trimethylsilylethyl, aralkylsilyl groups such as tert-butydiphenylsilyl (TBDPS), cyclic acetals such as isopropylidene-, cyclopentylidene-, cyclohexylidene-, benzylidene-, p-methoxybenzylidene- or o,p-dimethoxybenzylideneacetal, acyclic acetals such as tetrahydropyranyl (Thp), methoxymethyl (MOM), methoxyethoxymethyl (MEM), benzyloxymethyl (BOM) or methylthiomethyl (MTM). Acyl groups having 2 to 5 C atoms, such as acetyl, propionyl, butyryl and pivaloyl, are particularly preferred as hydroxy protecting group in the compounds of formula I according to the invention.

The compounds of formula I can otherwise be prepared by methods known per se, such as those described in the literature (e.g. in the standard works such as Houben-Weyl, Methoden der Organisschen Chemie (Methods of Organic Chemistry), Georg-Thieme-Verlag, Stuttgart), namely under reaction conditions such as those which are not mentioned in greater detail herein.

The compounds of formula II and III are known; the unknown compounds of formula II or III can easily be prepared analogously to the known compounds, e.g. those described in the examples of U.S. Pat. No. 5,767,132.

The reaction of the compounds of formulae II and III proceeds according to methods such as those known from the literature for the alkylation of amines. The components can be melted together in the absence of a solvent, in a sealed tube or an autoclave if necessary. It is also possible, however, to react the compounds in the presence of an inert solvent. Examples of suitable solvents are hydrocarbons, such as benzene, toluene or xylene; ketones such as acetone or butanone, ethers such as tetrahydrofuran or dioxane, amides such as dimethylformamide or n-methylpyrrolidone, or nitrites such as acetonitrile, o else, if desired mixtures of these solvents with one another or mixtures with water. It can be favourable to add an acid-binding agent, for example an alkali metal or alkaline earth metal hydroxide, carbonate or bicarbonate or another alkali metal or alkaline earth metal salt of a weak acid, preferably a potassium, sodium or calcium salt, or to add an organic base such as triethylamine, dimethylaniline, pyridine or quinoline, or an excess of he amine compound. The reaction time is between a few minutes and 14 days, depending on the conditions used, and the reaction temperature is between about 0 and 150° C., normally between 20 and 130° C.

Preferred compounds in the context of the invention are those of the general formula I

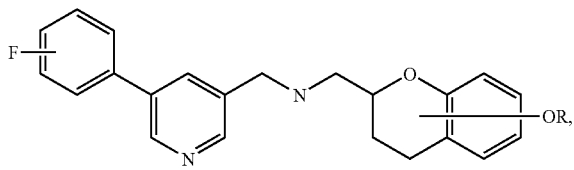

I where

OR is in the 4-, 7-, or 8-position of the chromane system and F is in the 4-position of the phenyl ring.

Therefore, preferred compounds are 2-({([5-(4-fluorophenyl)-pyridin-3ylmethyl]-amino}-methyl)-chroman-4-ol, 2-({[5-(4-fluorophenyl)-pyridin-3ylmethyl]-amino}-methyl)-chroman-7-ol, 2-({[5-(4-fluorophenyl)-pyridin-3ylmethyl]-amino}-methyl)-chroman-8-ol, or their optical isomers or physiologically acceptable salts or solvates, such as a) (2R/S),4R/S)-2-({[5-(4-fluorophenyl)-pyridin-3ylmethyl]-amino}-methyl)-chroman-4-ol,
b) (2S,4R/S)-2-({[5-(4-fluorophenyl)-pyridin-3ylmethyl]-amino}-methyl)-chroman-4-ol,
c) (2S,4R)-2-({[5-(4-fluorophenyl)-pyridin-3ylmethyl]-amino}-methyl)-chroman-4-ol,
d) (2S,4S)-2-({[5-(4-fluorophenyl)-pyridin-3ylmethyl]-amino}-methyl)-chroman-4-ol,
e) (2R,4R/S)-2-({[5-(4-fluorophenyl)-pyridin-3ylmethyl]-amino}-methyl)-chroman-4-ol,
f) (2R,4R)-2-({[5-(4-fluorophenyl)-pyridin-3ylmethyl]-amino}-methyl)-chroman-4-ol,
g) (2R,4S)-2-({[5-(4-fluorophenyl)-pyridin-3ylmethyl]-amino}-methyl)-chroman-4-ol,
h) (2R/S)-2-({[5-(4-fluorophenyl)-pyridin-3ylmethyl]-amino}-methyl)-chroman-7-ol,
i) (2R)-2-({[5-(4-fluorophenyl)-pyridin-3ylmethyl]-amino}-methyl)-chroman-7-ol,
j) (2S)-2-({[5-(4-fluorophenyl)-pyridin-3ylmethyl]-amino}-methyl)-chroman-7-ol,
k) (2R/S)-2-({[5-(4-fluorophenyl)-pyridin-3ylmethyl]-amino}-methyl)-chroman-8-ol,
l) (2R)-2-({[5-(4-fluorophenyl)-pyridin-3ylmethyl]-amino}-methyl)-chroman-8-ol,
m) (2S)-2-({[5-(4-fluorophenyl)-pyridin-3ylmethyl]-amino}-methyl)-chroman-8-ol, or a physiologically acceptable salt or solvate thereof.

Particularly preferred compounds of formula I are the compounds selected from the group consisting of a) (2R/S),4R/S)-2-({[5-(4-fluorophenyl)-pyridin-3ylmethyl]-amino}-methyl)-chroman-4-ol,
b) (2S,4R/S)-2-({[5-(4-fluorophenyl)-pyridin-3ylmethyl]-amino}-methyl)-chroman-4-ol,
c) (2S,4R)-2-({[5-(4-fluorophenyl)-pyridin-3ylmethyl]-amino}-methyl)-chroman-4-ol,
d) (2S,4S)-2-({[5-(4-fluorophenyl)-pyridin-3ylmethyl]-amino}-methyl)-chroman-4-ol,
e) (2R,4R/S)-2-({[5-(4-fluorophenyl)-pyridin-3ylmethyl]-amino}-methyl)-chroman-4-ol,
f) (2R,4R)-2-({[5-(4-fluorophenyl)-pyridin-3ylmethyl]-amino}-methyl)-chroman-4-ol,
g) (2R,4S)-2-({[5-(4-fluorophenyl)-pyridin-3ylmethyl]-amino}-methyl)-chroman-4-ol, or a physiologically acceptable salt or solvate thereof.

The most particularly preferred compound of formula I is (2R,4R)-2-({[5-(4-fluorophenyl)-pyridin-3ylmethyl]-amino}-methyl)-chroman-4-ol or a physiologically acceptable salt or solvate thereof.

In the context of the present invention, the aminomethyl chroman compounds of formula I can be present in various stereoisomeric forms, i.e. in the form of their (+) or (−) enantiomers or as a mixture of these enantiomers (racemate). For the separation of the racemates into the enantiomeric forms, reference is made to the relevant, known specialist literature.

In the context of the present invention, the physiologically acceptable salts can also be employed. Physiologically acceptable salts of the substituted 2-aminomethyl chromans of formula I can be salts of the compounds according to the invention with suitable organic or inorganic acids, in particular mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalene-disulphonic acid, acetic acid, propionic acid, lactic acid, tartaric acid, citric aid, fumaric acid, maleic acid or benzoic acid.

A preferred salt of 2-({[5-(4-fluorophenyl)-pyridin-3ylmethyl]-amino}-methyl)-chroman-4-ol or its optical isomers is the monohydrochloride or the monohydrochloride hemihydrate.

A preferred salt of 2-({[5-(4-fluorophenyl)-pyridin-3ylmethyl]-amino}-methyl)-chroman-7-ol or its optical isomers is the hydrobromide or the maleate.

A preferred salt of 2-({[5-(4-fluorophenyl)-pyridin-3ylmethyl]-amino}-methyl)-chroman-8-ol or its optical isomers is the hydrobromide or the maleate.

The invention had the object of providing novel uses for substituted aminomethyl chromans of formula I, their optical isomers and/or their physiologically acceptable salts and solvates.

It has been found that substituted aminomethyl chromans of formula I

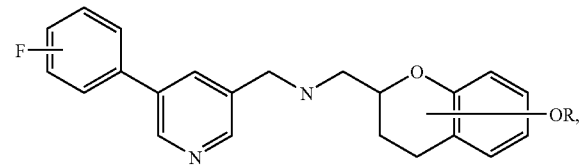

I in which

R represents hydrogen or a hydroxyl protecting group, and their optical isomers and pharmaceutically acceptable salts or solvates, in particular 2-({[5-(4-fluorophenyl)-pyridin-3ylmethyl]-amino}-methyl)-chroman-4-ol, 2-({[5-(4-fluorophenyl)-pyridin-3ylmethyl]-amino}-methyl)-chroman-7-ol, 2-({[5-(4-fluorophenyl)-pyridin-3ylmethyl]-amino}-methyl)-chroman-8-ol, or an optical isomer or a physiologically acceptable salt or solvate thereof, have therapeutic activity against extrapyramidal movement disorders such as idiopathic Parkinsons's disease, Parkinson syndromes, dyskinetic, choreatic, or dystonic syndromes, tremor, Gilles de la Torette syndrome, ballism, myoclonus, restless legs syndrome or Wilsons's disease, as well as extrapyramidal motoric disturbances [synonymous extrapyramidal symptoms (EPS)] induced by neuroleptics.

Additionally it has been found that substituted aminomethyl chromanes of formula I

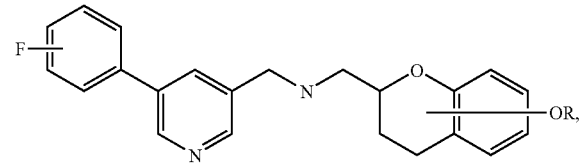

I in which

R represents hydrogen or a hydroxyl protecting group, and their optical isomers and pharmaceutically acceptable salts or solvates, in particular 2-({[5-(4-fluorophenyl)-pyridin-3ylmethyl]-amino}-methyl)-chroman-4-ol, 2-({[5-(4-fluorophenyl)-pyridin-3ylmethyl]-amino}-methyl)-chroman-7-ol, 2-({[5-(4-fluorophenyl)-pyridin-3ylmethyl]-amino}-methyl)-chroman-8-ol, or an optical isomer or a physiologically acceptable salt or solvate thereof, have therapeutic activity against adverse effects of anti-Parkinsonian drugs in extrapyramidal movement disorders, in particular against dopaminomimetic adverse effects of anti-Parkinsonian drugs in idiopathic Parkinson's disease or Parkinson syndromes.

It has been found that substituted aminomethyl chromans of formula I

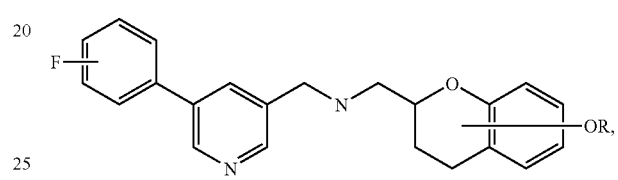

I in which

R represents hydrogen or a hydroxyl protecting group, and their optical isomers and pharmaceutically acceptable salts, in particular 2-({[5-(4-fluorophenyl)-pyridin-3ylmethyl]-amino}-methyl)-chroman-4-ol or an optical isomer or a physiologically acceptable salt or solvate thereof, excert an extraordinary potency in reversing catalepsy. Extrapyramidal motor side effects in e.g. rodents are measured by the ability of a drug to induce catalepsy. Catalepsy is defined as a state where an animal continues to remain in an unnormal (non-physiological 'uncomfortable') posture for a long time (e.g.: M. E. Stanley and S. D. Glick, Neuropharmacology, 1996; 15: 393-394; C. J. E. Niemegeers and P. Janssen, Life Sci., 1979, 201-2216). For example, if a hindpaw of a rat is placed on an elevated level, e.g. a platform elevated 3 cm above ground level, a normal rat immediately withdraws the hindpaw from the platform to the ground level. A cataleptic rat remains in this unnatural posture even for minutes.

Beneficial effects on the extrapyramidal motoric system have previously been described for other drugs with 5-HT$_{1A}$ agonistic action. Buspirone for example, which is an anxiolytic drug by nature, exhibits moderate anti-dyskinetic properties in advanced Parkinson patients (B. Kleedorfer et al., J Neurol Neurosurg Psychiatry, 1991, 54: 376-377; V. Bonifati et al., Clin Neuropharmacol, 1994, 17: 73-82). The main mechanism of action is obviously via stimulation of 5-HT$_{1A}$ receptors of the raphe nigral and raphe striatal pathways.

Likewise, the antipsychotic drug clozapine, which has very high affinity for the dopamine D4 but also for a variety of other receptors, has demonstrated beneficial antidyskinetic effects in Parkinson patients (e.g. Durif F et al., Neurology 1997; 48: 658-662). More recently, the experimental compound 8-methyl-6-(4-methyl-1-piperazineyl)-11H-pyrido[2,3-b][1,4,]benzodiazepine, a structural analog of clozapine with much increased selectivity for the dopamine D4 receptor compared to clozapine itself (Liegeois J F et al., Eur. J. Pharmacol. 1995; 273: R1-R3), has been demonstrated to have beneficial effects in parkinsonian monkeys (Tahar A H et al., Eur. J. Pharmacol. 2000; 399: 183-186).

In rats, the subcutaneous $ED_{50}$ value (i.e. the calculated dose to reverse catalepsy by 50%) for (2R,4R)-2-({[5-(4-fluorophenyl)-pyridin-3ylmethyl]-amino}-methyl)-chroman-4-ol is about 2 mg/kg which is comparable or even more potent compared to other 5-$HT_{1A}$ agonists such as ipsapirone ($ED_{50}$ 10 mg/kg) or buspirone ($ED_{50}$ 6 mg/kg) and the D4 antagonist 8-methyl-6-(4-methyl-1-piperazineyl)-11 H-pyrido[2,3-b][1,4,]benzodiazepine ($ED_{50}$ 3 mg/kg).

Therefore, the present invention relates to the use of substituted aminomethyl chromans of formula I and their optical isomers and pharmaceutically acceptable salts or solvates for the manufacture of a medicament for the treatment of extrapyramidal movement disorders.

Therefore, the invention especially relates to the use of (2R,4R)-2-({[5-(4-flurophenyl)-pyridin-3ylmethyl]-amino}-methyl)-chroman-4-ol or a pharmacologically acceptable salt or solvate for the manufacture of a medicament for the treatment of extrapyramidal movement disorders.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of extrapyramidal movement disorders in which the pharmacologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least (2R,4R)-2-({[5-(4-fluorophenyl)-pyridin-3ylmethyl]-amino}-methyl)-chroman-4-ol or one of its biocompatible salts or solvates for the treatment of extrapyramidal movement disorders.

A compound of formula I according to claim 1 or a physiologically acceptable salt or solvate thereof, useful for the treatment of extrapyramidal movement disorders, in particular for the treatment of idiopathic Parkinson's disease, Parkinson syndromes, dyskinetic, choreatic or dystonic syndromes, extrapyramidal motoric adverse effects of neuroleptics, tremor, Gilles de la Tourette syndrome, ballism, myoclonus, restless legs syndrome or Wilson's disease and/or useful for the treatment of adverse effects in idiopathic Parkinson's disease or Parkinson syndromes including medicinal compositions as defined below, is preferably administered in doses from 0.1 to 100 mg, preferentially between approximately 1 and 20 mg. The composition may be administered once or more times a day, e.g. 2, 3, or 4 times daily. The specific dose for each patient depends on all sorts of factors, e.g. on the activity of the specific compound employed, on the age, body weight, general state of health, on sex, diet, time and route of administration, on the excretion rate, pharmaceutical substance combination and on the severity of the particular disorder to which the therapy relates. Oral administration is preferred, but also parenteral routes of administration (e.g. intravenous or transdermal) can be utilized.

Anti-Parkinsonian drugs are conventional drugs such as l-dopa (levodopa) and l-dopa combined with a decarboxylase inhibitor such as benserazide or carbidopa, dopamine agonists such as bromocriptine, apomorphine, cabergoline, pramipexol, ropinirol, pergolide, dihydro-α-ergocriptine or lisuride plus all drugs acting via stimulation of dopamine receptors, inhibitors of catechol-O-methyl transferase (COMT) such as entacapone or tolcapone, inhibitors of monoamine oxidase (MAO) such as selegiline and antagonists of N-methyl-D-aspartate (NMDA) receptors such as amantadine or budipine.

Adverse effects of said anti-Parkinsonian drugs are all types of dyskinesias, such as choreic, dystonic, ballistic and myoclonic dyskinesia, as well as motor (response) fluctuations or psychotic states, such as optical or acoustical hallucinations.

Therefore, the present invention relates to the use of substituted aminomethyl chromans of formula I and their optical isomers and pharmaceutically acceptable salts or solvates for the manufacture of a medicament for the treatment of adverse effects of anti-Parkinsonian drugs in idiopathic Parkinson's disease.

Therefore, the invention especially relates to the use of (2R,4R)-2-({[5-(4-fluorophenyl)-pyridin-3ylmethyl]-amino}-methyl)-chroman-4-ol or a pharmacologically acceptable salt or solvate for the manufacture of a medicament for the treatment of adverse effects of anti-Parkinsonian drugs in idiopathic Parkinson's disease.

Treatment of adverse effects of conventional anti-Parkinsonian drugs as defined above are determined in a modification of the animal model of the Parkinsonian cynomolgus monkey according to P. J. Blanchet et al., Exp. Neurology 1998; 153: 214-222. Monkeys render parkinsonian by repeated injections of 1-methyl-4-phenyl-1,2,3,6-tetrahydropyridine (MPTP). The Parkinsonian monkeys are chronically treated with the standard 1-dopa therapy according to P. J. Blanchet et al., Mov. Disord., 1998; 13: 798-802. Longterm treatment with l-dopa induces extrapyramidal motor side effects and psychotic states which are both qualitatively and quantitatively, assessed by the Abnormal Involuntary Movement Scale (P. J. Blanchet et al., Mov. Disord. 1998; 13: 798-802) for different body parts (face, neck, trunk, each limb) and by rating for psychotic states by observing the monkey's attention, reactivity and mobility. (2R,4R)-2-({[5-(4-fluorophenyl)-pyridin-3ylmethyl]-amino}-methyl)-chroman-4-ol reduce overall choreiform dyskinesias and dystonic dyskinesias as well as psychotic states.

A typical study to investigate the efficacy of the compounds according to the invention for adverse effects in Parkinson's disease is described in the following. 40 patients of either sex with advanced idiopathic Parkinson's disease complicated by "peak-dose" dyskinesia participate in a double-blind study. The main inclusion criteria are Hoehn & Yahr stage $\geq 2.5$ (lit.: Hoehn H. M. et al, Neurology 1967; 17: 427-442), aged 40-75 years, symptom duration of at least 5 years, and a l-dopa treatment duration of at least 3 years. (2R,4R)-2-({[5-(4-fluorophenyl)-pyridin-3ylmethyl]-amino}-methyl)-chroman-4-ol monohydrochloride hemihydrate or placebo is administered as "add on" to the conventional Parkinson treatment, which is maintained unchanged during the whole study. The dose of blinded medication is titrated over a period of 3 weeks in a range from 2.5 to 10 mg b.i.d. Then the medication is kept constant for 3 weeks. Before the start of titration and at the end of the treatment period the patients fill a diary card in 30 min. inervals for 48 hours. The diary card differentiates 5 different states: (1) "on" without dyskinesia, (2) "on" with troublesome dyskinesia, (3) "on" with non-troublesome dyskinesia, (4) "off" time, and (5) time asleep (Hauser R A et al., Clin. Neuropharmacol., 2000, 23, 75-81). The primary outcome variable of the protocol is the change in "on" time with troublesome dyskinesia. The statistical analysis of the diary data demonstrates a significant reduction in "on" time with troublesome dyskinesia under treatment with (2R,4R)-2-({[5-(4-fluorophenyl)-pyridin-3ylmethyl]-amino}-methyl)-chroman-4-ol monohydrochloride hemihydrate while the "on" time without dyskinesia significantly increase. The other parameters are not changed.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of adverse effects of anti-Parkinsonian drugs in idiopathic Parkinson's disease in which the pharmacologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenylpyridin-3ylmethyl]-amino}-methyl)-chroman-4-ol or one of its biocompatible salts or solvates for the treatment of adverse effects of anti-Parkinsonian drugs in idiopathic Parkinson's disease.

Furthermore, the present invention relates to the use of substituted aminomethyl chromans of formula I and their optical isomers and pharmaceutically acceptable salts or solvates for the manufacture of a medicament for the treatment of idiopathic Parkinson's disease.

Therefore, the invention especially relates to the use of (2R,4R)-2-({[5-(4-fluorophenyl)-pyridin-3ylmethyl]-amino}-methyl)-chroman-4-ol or a pharmacologically acceptable salt or solvate for the manufacture of a medicament for the treatment of idiopathic Parkinson's disease.

A typical animal model for idiopathic Parkinson's disease is the Parkinsonian cynomolgus monkey according to P. J. Blanchet et al., Exp. Neurology 1998; 153: 214-222. Monkeys render parkinsonian by repeated injections of 1-methyl-4-phenyl-1,2,3,6-tetrahydropyridine (MPTP). Parkinsonian symptoms are qualitatively assessed by the use of the Laval University Disability Scale (B. Gomez-Mancilla et al., 1993; Mov. Disord. 8: 144-150) measuring the following symptoms: posture, mobility, climbing, gait, holding food, vocalizing, grooming, social interaction. (2R,4R)-2-({[5-(4-fluorophenyl)-pyridin-3ylmethyl]-amino}-methyl)-chroman-4-ol reduce all the parkinsonian symptoms and increased total activity.

A typical study to investigate the efficacy of the compounds according to the invention in the treatment of idiopathic Parkinson's disease is described in the following. 180 patients of either sex with idiopathic Parkinson's disease participate in a double-blind study. The main inclusion criteria are Hoehn & Yahr stage ≧2.0 (Hoehn H. M. et al, Neurology 1967; 17: 427442), aged 50-80 years, symptom duration of at least 5 years. (2R,4R)-2-({[5-(4-fluorophenyl)-pyridin-3ylmethyl]-amino}-methyl)-chroman-4-ol monohydrochloride hemihydrate or placebo is administered as "add on" to the conventional Parkinson treatment, which is maintained unchanged during the whole study. The dose of blinded medication is titrated over a period of 4 weeks in a range from 2.5 to 10 mg b.i.d. Then the medication is kept constant for 1 week. Before the start of titration and at the end of the treatment period the patients fill a diary card in 30 min. intervals for 48 hours. The diary card differentiates 5 different states: (1) "on" without dyskinesia, (2) "on" with troublesome dyskinesia, (3) "on" with non-troublesome dyskinesia, (4) "off" time, and (5) time asleep (Hauser R A et al., Clin. Neuropharmacol., 2000, 23, 75-81). This allows to detect simultaneously a beneficial effect of (2R,4R)-2-({[5-(4-fluorophenyl)-pyridin-3ylmethyl]-amino}-methyl)-chroman-4-ol or a physiologically acceptable salt or solvate thereof, in particular of (2R,4R)-2-({[5-(4-fluorophenyl)-pyridin-3ylmethyl]-amino}-methyl)-chroman-4-ol monohydrochloride hemihydrate, on the global motoric function, on dystonia, motor fluctuations, and on psychosis. Furthermore, the efficacy to treat tremor is shown. The analysis demonstrates a significant clinical improvement under treatment with (2R,4R)-2-({[5-(4-fluorophenyl)-pyridin-3ylmethyl]-amino}-methyl)-chroman-4-ol monohydrochloride hemihydrate.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of idiopathic Parkinson's disease in which the physiologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenyl)-pyridin-3ylmethyl]-amino}-methyl)-chroman-4-ol or one of its biocompatible salts or solvates together with at least one solid, liquid or semiliquid excipient or adjunct for the treatment of idiopathic Parkinson's disease.

The limiting factor of Parkinson treatment with l-dopa and/or dopamine agonists is often the occurence of psychosis or dyskinesia and other motor fluctuations.

It has been found that compounds of formula I according to claim 1 or physiologically acceptable salts or solvates thereof enhance the anti-Parkinsonian effect of anti-Parkinsonian drugs as defined above without inducing extrapyramidal side effects.

Therefore, the add-on therapy with in particular (2R,4R)-2-({[5-(4-fluorophenyl)-pyridin-3ylmethyl]-amino}-methyl)-chroman-4-ol or a pharmaceutically acceptable salt or solvate thereof, in particular of (2R,4R)-2-({[5-(4-fluorophenyl)-pyridin-3ylmethyl]-amino}-methyl)-chroman-4-ol monohydrochloride hemihydrate, now opens the possibility to increase the doses of l-dopa and/or dopamine agonists and/or all other anti-Parkinsonian drugs as defined above in order to counteract periods of insufficient motility ("off" phases) without provoking the above mentioned side effects. That represents an entirely novel approach in the treatment of Parkinson's disease leading to a significant benefit for the patients.

Thus, the invention relates to a pharmaceutical composition comprising, as active principles, (i) a compound according to claim 11 or 12, and (ii) at least one anti-Parkinsonian drug, in combination with one or more pharmaceutically acceptable excipients.

Particularly, the invention relates to a pharmaceutical composition comprising, as active principles, (i) (2R,4R)-2-({[5-(4-fluorophenyl)-pyridin-3ylmethyl]-amino}-methyl)-chroman-4-ol or a pharmaceutically acceptable salt or solvate, and (ii) l-dopa.

Thus, the invention relates to a pharmaceutical composition comprising, as active principles, (i) a compound according to claim 11 or 12, (ii) at least one anti-Parkinsonian drug, and at least (iii) one decarboxylase inhibitor, in combination with one or more pharmaceutically acceptable excipients.

Particularly, the invention relates to a pharmaceutical composition comprising, as active principles, (i) (2R,4R)-2-({[5-(4-fluorophenyl)-pyridin-3ylmethyl]-amino}-methyl)-chroman-4-ol or a pharmaceutically acceptable salt or solvate, (ii) l-dopa and (iii) benserazide or carbidopa, in combination with one or more pharmaceutically acceptable excipients.

The ratios of the respective amounts of a compound according to claim 11 or 12 and of the conventional anti-Parkinsonian drug, optionally together with an decarboxylase inhibitor thus vary in consequences. Preferably, the weight ratio of (2R,4R)-2-({[5-(4-fluorophenyl)-pyridin-3ylmethyl]-amino}-methyl)-chroman-4-ol or one of its physiologically acceptable salts or solvates to the conventional anti-Parkinsonian drug ranges from 1:1 to 1:100, preferably from 1:10 to 1:90 and better still from 1:40 to 1:60.

Another subject of the present invention is additionally the use of a compound of formula I according to claim 1, in particular of (2R,4R)-2-({[5-(4-fluorophenyl)-pyridin-3ylmethyl]-amino}-methyl)-chroman-4-ol or one of its physiologically acceptable salts or solvates, in combination with at least one anti-Parkinsonian drug, for the preparation of a medicinal combination intended to enhance the anti-Parkinsonian effect of said anti-Parkinsonian drugs.

According to the invention, the term "medicinal combination" is intended to refer either to a pharmaceutical composition as defined above, in which the two active principles or compounds are the essential constituents of the same composition, or to a kit comprising two separate compositions, the first comprising for example (2R,4R)-2-({[5-(4-fluorophenyl)-pyridin-3ylmethyl]-amino}-methyl)-chroman-4-ol or one of its physiologically acceptable salts or solvates as sole active principle, and the second comprising at least one anti-Parkinsonian drug as active compound.

When the medicinal combination is in the form of a kit, the administration of the two compositions constituting this kit, although carried out separately, is simultaneous for a combined therapy. It is preferred to use (2R,4R)-2-({[5-(4-fluorophenyl)-pyridin-3ylmethyl]-amino}-methyl)-chroman-4-ol in the form of the monohydrochloride hemihydrate.

Adverse effects of anti-Parkinsonian drugs as defined above are additionally known in particular in Parkinson syndromes.

Parkinson syndromes are e.g. multiple system atrophies (MSA), Steele-Richardson-Olszewski syndrome (=progressive supranuclear palsy), cortico-basal degeneration, olivo-ponto cerebellar atrophy or Shy Drager syndrome.

Therefore, the invention relates to the use of substituted aminomethyl chromans of formula I and their optical isomers and pharmaceutically acceptable salts or solvates for the manufacture of a medicament for the treatment Parkinson syndromes and/or for the treatment of adverse effects of anti-Parkinsonian drugs in Parkinson syndromes.

Therefore, the invention especially relates to the use of (2R,4R)-2-({[5-(4-fluorophenyl)-pyridin-3ylmethyl]-amino}-methyl)-chroman-4-ol or a pharmacologically acceptable salt or solvate for the manufacture of a medicament for the treatment of Parkinson syndromes and/or for the treatment of adverse effects of anti-Parkinsonian drugs in Parkinson syndromes.

A typical animal model is the reserpinized rat or mouse (e.g. M. S. Starr and B. S. Starr, J. Neural Transm.—Park. Dis. Dement. Sect., 1994; 7: 133-142; M. Gossel et al., J. Neural Transm.—Park. Dis. Dement. Sect., 1995; 10: 27-39; N. R. Hughes et al., Mov. Disord., 1998; 13: 228-233). Reserpine is a potent depleter of monoamines and produces nearly complete akinesia in both species. Prominent 24 h after application, the distance travelled and the time active is nearly zero as measured in conventional activity meters. (2R,4R)-2-({[5-(4-fluorophenyl)-pyridin-3ylmethyl]-amino}-methyl)-chroman-4-ol or a pharmaceutically acceptable salt or solvate thereof dose-dependently reduce akinesia, i.e. restored distance travelled and time active to about the level of normal animals.

Another more recent animal model is the striatonigral degeneration approach in the rat according to G. K. Wenning et al., J. Neural Transm. Suppl., 1999; 55: 103-113. Rats receive an unilateral injection of 6-hydroxydopamine into the left medial forebrain bundle followed by an injection of quinolinic acid into the ipsilateral striatum inducing nigrostriatal degeneration. The degeneration results in turning behavior to a challenge with dopaminomimetics such as apomorphine or amphetamine. Turning behavior is measured by an automated recorder. Turning behavior induced by apomorphine or amphetamine is dose-dependently antagonized by (2R,4R)-2-({[5-(4-fluorophenyl)-pyridin-3ylmethyl]-amino}-methyl)-chroman-4-ol or a pharmaceutically acceptable salt or solvate thereof.

Multiple system atrophy (MSA) is due to an expansive neurodegeneration in the extrapyramidal and autonomic nervous system which leads to an akinetic Parkinsonian syndrome with vegetative disturbances. In contrast to idiopathic Parkinson's disease the density of central dopamine receptors is markedly decreased and therefore, MSA patients poorly respond to dopaminergic drugs. Since (2R,4R)-2-({[5-(4-fluorophenyl)-pyridin-3ylmethyl]-amino}-methyl)-chroman-4-ol or a pharmaceutically acceptable salt or solvate thereof act predominantly via serotonin receptors on the extrapyramidal system, they are able to improve the motor performance in these otherwise mostly untreatable patients.

A typical study to investigate the efficacy of the compounds according to the invention in MSA patients encompasses 30 patients of either sex with a symptom duration of at least 5 years and a significant reduction of central dopamine receptors in positron emission tomography (PET) scan. The study design is similar to that described above for Parkinson's disease. (2R,4R)-2-({[5-(4-fluorophenyl)-pyridin-3ylmethyl]-amino}-methyl)-chroman-4-ol monohydrochloride hemihydrate or placebo is titrated as "add on" to the conventional treatment (dose range 2,5 to 20 mg b.i.d.). After a double-blind dose-finding phase of 3 weeks during which the individual dose is identified for each patient on the basis of tolerability and efficacy, the dose is maintained unchanged for 3 additional weeks. Before the start of titration and at the end of the treatment period a complete UPDRS assessment is performed in each patient (primary outcome measure). Statistical analysis of UPDRS demonstrates a significant clinical improvement of Parkinson symptoms under treatment with (2R,4R)-2-({[5-(4-fluorophenyl)-pyridin-3ylmethyl]-amino}-methyl)-chroman-4-ol monohydrochloride hemihydrate.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of Parkinson syndromes and/or for the treatment of adverse effects of anti-Parkinsonian drugs in Parkinson syndromes in which the pharmacologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenyl)-pyridin-3ylmethyl]-amino}-methyl)-chroman-4-ol or one of its biocompatible salts or solvates for the treatment of Parkinson syndromes and/or for the treatment of adverse effects of anti-Parkinsonian drugs in Parkinson syndromes.

The present invention relates furthermore to the use of substituted aminomethyl chromans of formula I and their optical isomers and pharmaceutically acceptable salts or solvates for the manufacture of a medicament for the treatment of dyskinetic and/or choreatic syndromes.

Therefore, the invention especially relates to the use of (2R,4R)-2-({[5-(4-fluorophenyl)-pyridin-3ylmethyl]-amino}-methyl)-chroman-4-ol or a pharmacologically acceptable salt or solvate for the manufacture of a medicament for the treatment of dyskinetic and/or choreatic syndromes.

Dyskinetic and/or choreatic syndromes are e.g. Huntington's disease, minor chorea or chorea of pregnancy. (2R,4R)-2-({[5-(4-fluorophenyl)-pyridin-3ylmethyl]-amino}-methyl)-chroman-4-ol or a physiologically acceptable salt or solvate thereof are in particular useful for the treatment of Huntington's disease.

A typical animal model is the systemic 3-nitropropionic acid (3-NP) model in rats according to C. V. Borlongan et al., Brain Res., 1995; 697: 254-257. Rats are treated with injections of the selective striatal neurotoxin 3-NP i.p. every fourth day (C. V. Borlongan et al., Brain Res. Protocols, 1997; 1: 253-257). After two injections of 3-NP, rats display nocturnal hyperactivity reflecting symptoms of early Huntington's disease, whereas rats treated with four injections of 3-NP display nocturnal akinesia (hypoactivity) reflecting symptoms of late Huntington's disease. Nocturnal activity is automatically measured in conventional acitivity cages by infrared beams. (2R,4R)-2-({[5-(4-fluorophenyl)-pyridin-3ylmethyl]-amino}-methyl)-chroman-4-ol or a pharmaceutical acceptable salt or solvate thereof reduce both the nocturnal hyperactivity and akinesia.

A typical trial to establish the effect of the compounds according to the invention on chorea, voluntary motor performance, and functional disability in patients with Huntington's disease encompasses 32 genetically diagnosed patients. (2R,4R)-2-({[5-(4-fluorophenyl)-pyridin-3ylmethyl]-amino}-methyl)-chroman-4-ol monohydrochloride hemihydrate or placebo is administered as "add on" to the conventional treatment, which is maintained unchanged during the whole study. The dose of blinded medication is titrated over a period of 3 weeks in a range from 2.5 to 20 mg b.i.d. Then the medication is held constant for 1 week. Assessments are performed in the week before and at the last day of the trial. Chorea is scored using the abnormal involuntary movement scale (AIMS, W. Guy, in: ECDEU assessment manual. Rockville Md.: US dept. of health, education and welfare, 1976: 534-537), the unified Huntington's disease rating scale (UH-DRS, Huntington study group, 1996, Movement Disord, 11: 13642), and judgement of video recordings. Voluntary motor performance is assessed using the UHDRS motor scale. Patients and their partners complete a questionnaire regarding functional disability. Statistical analysis demonstrates significant improvement of voluntary and involuntary motor performance in Huntington patients under treatment with (2R,4R)-2-({[5-(4-fluorophenyl)-pyridin-3ylmethyl]-amino}-methyl)-chroman-4-ol or a physiologically acceptable salt thereof.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of dyskinetic and/or choreatic syndromes, in particular for the treatment of Huntington's disease, in which the pharmacologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenyl)-pyridin-3ylmethyl]-amino}-methyl)-chroman-4-ol or one of its biocompatible salts or solvates for the treatment of dyskinetic and/or choreatic syndromes.

The present invention relates to the use of substituted aminomethyl chromans of formula I and their optical isomers and pharmaceutically acceptable salts or solvates for the manufacture of a medicament for the treatment of dystonic syndromes.

Therefore, the invention especially relates to the use of (2R,4R)-2-({[5-(4-fluorophenyl)-pyridin-3ylmethyl]-amino}-methyl)-chroman-4-ol or a pharmacologically acceptable salt or solvate for the manufacture of a medicament for the treatment of dystonic syndromes.

Dystonic syndromes are e.g. spasmalic torticollis, writer's cramp, blepharospasm, Meige syndrome or dopasensitive dystonia. (2R,4R)-2-({[5-(4-fluorophenyl)-pyridin-3ylmethyl]-amino}-methyl)-chroman-4-ol or a physiologically acceptable salt or solvate thereof is in particular useful for the treatment of spasmalic torticollis and/or blepharospasm.

A typical animal model is the mutant dystonic hamster according to A. Richter and W. Löscher, Prog. Neurobiol. 1998; 54: 633-677. In this genetically dystonic hamsters, dystonic attacks are provoked by taking the animal from the home cage and placing it on a balance. The dystonic syndrome consists of a sequence of abnormal movements, and the severity of the single symptoms is rated by a scoring system. (2R,4R)-2-({[5-(4-fluorophenyl)-pyridin-3ylmethyl]-amino}-methyl)-chroman-4-ol or a pharmaceutically acceptable salt or solvate thereof dose-dependently reduce the severity of dystonic symptoms.

To demonstrate the efficacy of the compounds according to the invention in dystonic syndromes, a double-blind, placebo-controlled study is performed in patients with cervical dystonia (spasmodic torticollis) who do not tolerate injection of botulinum toxin. (2R,4R)-2-({[5-(4-fluorophenyl)-pyridin-3ylmethyl]-amino}-methyl)-chroman-4-ol monohydrochloride hemihydrate is titrated as described above in the range from 2.5 mg to 20 mg b.i.d. The Toronto western spasmodic torticollis rating scale (TWSTRS, C. L. Comella et al., 1997, Movement Disord, 12: 570-575) is used as primary outcome measure. A significant improvement in the TWSTRS scores is noted for the patients treated with (2R,4R)-2-({[5-(4-fluorophenyl)-pyridin-3ylmethyl]-amino}-methyl)-chroman-4-ol or one of its pharmaceutically acceptable salts or solvates.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore the invention especially relates to the use for the manufacture of a medicament for the treatment of dystonic syndromes, in particular of spasmalic torticollis and/or blepharospasm, in which the pharmacologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenyl)-pyridin-3ylmethyl]-amino}-methyl)-chroman-4-ol or one of its biocompatible salts or solvates for the treatment of dystonic syndromes.

The present invention relates to the use of substituted aminomethyl chromans of formula I and their optical isomers and pharmaceutically acceptable salts or solvates for the manufacture of a medicament for the treatment of extrapyramidal symptoms induced by neuroleptics.

Therefore, the invention especially relates to the use of (2R,4R)-2-({[5-(4-fluorophenyl)-pyridin-3ylmethyl]- amino}-methyl)-chroman-4-ol or a pharmacologically acceptable salt or solvate for the manufacture of a medicament for the treatment of extrapyramidal symptoms induced by neuroleptics.

Extrapyramidal motoric disturbances induced by neuroleptics are e.g. early dyskinesia, dystonia, akathisia, parkinsonoid, in particular bradykinesia, or tardive dyskinesia. (2R,4R)-2-({[5-(4-fluorophenyl)-pyridin-3ylmethyl]-amino}-methyl)-chroman-4-ol or a physiologically acceptable salt or solvate thereof are useful particularly for the treatment of akathisia and/or tardive dyskinesia and/or parkinsonoid.

A typical animal model is neuroleptics-induced muscle rigidity in rats according to S. Wolfarth et al., Arch. Pharmacol. 1992; 345: 209-212. Rats are challenged with the conventional neuroleptic drug haloperidol which enhances muscle tone. Muscle tone is electromechanically measured as the resistence to passive flexion and extension of the hind limb. (2R,4R)-2-({[5-(4-fluorophenyl)-pyridin-3ylmethyl]-amino}-methyl)-chroman-4-ol or a pharmaceutically acceptable salt or solvate thereof decrease the muscle tone enhanced by haloperidol.

Another typical animal model is the neuroleptics sensitized monkey according to D. E. Casey, Psychopharmacology, 1996; 124: 134-140. Monkeys treated repeatedly with conventional neuroleptics are highly sensitive to a subsequent challenge dose of neuroleptic drugs. When challenged, the monkeys immediately show extrapyramidal motor side effects such as dystonia, dyskinesias, akathisia, and bradykinesia which are rated by a scoring system. The conventional neuroleptic drug haloperidol is given as a challenge. When the before-mentioned extrapyramidal motor side effects occur, (2R,4R)-2-({[5-(4-fluorophenyl)-pyridin-3ylmethyl]-amino}-methyl)-chroman-4-ol or a pharmaceutically acceptable salt or solvate thereof is administered; (2R,4R)-2-({[5-(4-fluorophenyl)-pyridin-3ylmethyl]-amino}-methyl)-chroman-4-ol dose-dependently reduce the extrapyramidal motor side effects.

Tardive dyskinesia is a common adverse effect of long-term treatment with neuroleptics. A typical study to investigate the efficacy of the compounds according to the invention in tardive dyskinesia is described in the following. 32 schizophrenic (DSM-III-R) inpatients aged 25-60 years on long-term stable antipsychotic treatment (duration of at least 5 years) entered the study. (2R,4R)-2-({[5-(4-fluorophenyl)-pyridin-3ylmethyl]-amino}-methyl)-chroman-4-ol monohydrochloride hemihydrate or placebo is administered as "add on" to the antipsychotic treatment, which is kept constant during the whole study. The dose of blinded medication is titrated over a period of 3 weeks in a range from 2,5 to 20 mg b.i.d. Then the medication is maintained under double-blind conditions for 2 weeks. After a 2-week wash-out period, the test drugs are crossed over. Assessments of tardive dyskinesia by means of the Abnormal Involuntary Movement Scale (AIMS, see above) and of Parkinsonian extrapyramidal side effects (UPDRS, see above) are made pretreatment and post-treatment. AIMS scores during treatment with (2R,4R)-2-({[5-(4-fluorophenyl)-pyridin-3ylmethyl]-amino}-methyl)-chroman-4-ol monohydrochloride hemihydrate are significantly lower than during placebo period.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of extrapyramidal symptoms induced by neuroleptics, in particular of akathisia and/or tardive dyskinesia, in which the pharmacologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenyl)-pyridin-3ylmethyl]-amino}-methyl)-chroman-4-ol or one of its biocompatible salts or solvates for the treatment of extrapyramidal symptoms induced by neuroleptics.

The present invention relates to the use of substituted aminomethyl chromans of formula I and their optical isomers and pharmaceutically acceptable salts or solvates for the manufacture of a medicament for the treatment of tremor.

Therefore, the invention especially relates to the use of (2R,4R)-2-({[5-(4-fluorophenyl)-pyridin-3ylmethyl]-amino}-methyl)-chroman-4-ol or a pharmacologically acceptable salt or solvate for the manufacture of a medicament for the treatment of tremor.

Tremor includes all types of tremors such as essential tremor, activated physiological tremor, cerebellar tremor, orthostatic tremor or drug-induced tremor. (2R,4R)-2-({[5-(4-fluorophenyl)-pyridin-3ylmethyl]-amino}-methyl)-chroman-4-ol or a physiologically acceptable salt or solvate thereof are particularly useful for the treatment of essential tremor and/or drug-induced tremor.

Typical animal models utilize either genetic mutant animals or are models where tremor is induced by a pharmacological agent (for review: H. Wilms et al., Mov. Disord., 1999; 14: 557-571).

Typical genetic models in mutant animals are the Campus Syndrome in the Pietrain pig according to A. Richter et al. (Exp. Neurology, 1995; 134: 205-213) or the Weaver mutant mouse according to J. R. Simon and B. Ghetti (Mol. Neurobiol., 1994; 9: 183-189). In the Campus Syndrome model, these mutant pigs show a high-frequency tremor when standing and during locomotion, but not while lying at rest. Assessment of tremor is made by accelerometric recording. In the Weaver mutant mouse, degenerative cerebellar atrophy is could in association with tremor, gait instability, and toppling over the sides after a few steps. Gait disability and toppling result in dramatically reduced locomotor activity measured by the distance travelled and the time spent with ambulation in conventional activity cages.

(2R,4R)-2-({[5-(4-fluorophenyl)-pyridin-3ylmethyl]-amino}-methyl)-chroman-4-ol or one of its pharmaceutically acceptable salts or solvates improve the Campus Syndrome in the Pietrain pig, i.e. reduce disabling tremor when standing and during locomotion, and enhance locomotor activity in the Weaver mutant mouse.

A typical animal model for drug-induced tremors is the oxotremorine-induced tremor (e.g. H. Hallberg and O. Almgren, Acta Physiol. Scand., 1987; 129: 407-13; J. G. Clement and W. R. Dyck, J. Pharmacol. Meth., 1989; 22: 25-36). Oxotremorine induces tremor which is measured by a rating scale. (2R,4R)-2-({[5-(4-fluorophenyl)-pyridin-3ylmethyl]-amino}-methyl)-chroman-4-ol or one of its pharmaceutically acceptable salts or solvates inhibit oxotremorine-induced tremors.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of tremors, in particular of essential tremors and/or drug-induced tremors, in which the pharmacologically acceptable salt is (2R,4R)-2-

({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenyl)-pyridin-3ylmethyl]-amino}-methyl)-chroman-4-ol or one of its biocompatible salts or solvates for the treatment of tremor.

The present invention relates to the use of substituted aminomethyl chromans of formula I and their optical isomers and pharmaceutically acceptable salts or solvates for the manufacture of a medicament for the treatment of extrapyramidal movement disorders chosen from the group consisting of Gilles de la Tourette syndrome, ballism, myoclonus, restless legs syndrome and Wilson's disease.

Therefore, the invention especially relates to the use of (2R,4R)-2-({[5-(4-fluorophenyl)-pyridin-3ylmethyl]-amino}-methyl)-chroman-4-ol or a pharmacologically acceptable salt or solvate for the manufacture of a medicament for the treatment of extrapyramidal movement disorders chosen from the group consisting of Gilles de la Tourette syndrome, ballism, myoclonus, restless legs syndrome and Wilson's disease.

A typical animal model for myoclonus is myoclonus induced by an acute hypoxic episode according to D. D. Truong et al., Mov. Dsiord., 1994; 9: 201-206). In this model of posthypoxic myoclonus, rats undergo a cardiac arrest for 8 minutes and are resuscitated thereafter. Myoclonic jerks occur spontaneously but can be provoked by auditory stimulation, too, worsening over the days following cardiac arrest. (2R,4R)-2-({[5-(4-fluorophenyl)-pyridin-3ylmethyl]-amino}-methyl)-chroman-4-ol or one of its pharmacologically acceptable salts or solvates dose-dependently reduce the number of spontaneous and autitory-evoked myoclonic jerks.

A preferred salt of (2R,4R)-2-({[5-(4-fluorophenyl)-pyridin-3ylmethyl]-amino}-methyl)-chroman-4-ol is (2R,4R)-2-({[5-(4-fluorophenyl)-pyridin-3ylmethyl]-amino}-methyl)-chroman-4-ol monohydrochloride hemihydrate.

Therefore, the invention especially relates to the use for the manufacture of a medicament for the treatment of extrapyramidal movement disorders chosen from the group consisting of Gilles de la Tourette syndrome, ballism, myoclonus, restless legs syndrome and Wilson's disease in which the pharmacologically acceptable salt is (2R,4R)-2-({[5-(4-fluorophenyl)-pyridin-3ylmethyl]-amino}-methyl)-chroman-4-ol monohydrochloride hemihydrate.

Additionally, the invention relates to the use of a pharmaceutical composition containing at least one compound of (2R,4R)-2-({[5-(4-fluorophenyl)-pyridin-3ylmethyl]-amino}-methyl)-chroman-4-ol or one of its biocompatible salts or solvates for the treatment of extrapyramidal movement disorders chosen from the group consisting of Gilles de la Tourette syndrome, ballism, myoclonus, restless legs syndrome and Wilson's disease.

The extrapyramidal movement disorders such as Steele-Richardson-Olszewski syndrome (=progressive supranuclear palsy), cortico-basal degeneration, olivo-ponto cerebellar atrophy, Shy Drager syndrome, minor chorea, chorea of pregnancy, writer's cramp, blepharospasm, Meige syndrome, dopa-sensitive dystonia, Gilles de la Tourette syndrome, ballism, myoclonus, restless legs syndrome, and Wilson's disease are not frequent enough to perform regular double-blind trials. However, the medical need in this field is pressing since no sufficient therapies are available so far.

Therefore, open-label observations in few selected patients are an adequate method to demonstrate the efficacy of (2R, 4R)-2-({[5-(4-fluorophenyl)-pyridin-3ylmethyl]-amino}-methyl)-chroman-4-ol or a physiologically acceptable salt or solvate thereof.

All the pharmaceutical preparations used for the treatment of extrapyramidal movement disorders and/or for the treatment of adverse effects of anti-Parkinsonian drugs in extrapyramidal movement disorders including the medicinal combination can be used as pharmaceuticals in human or veterinary medicine.

The compositions of the invention are preferably administered parenterally, or better still orally, although the other routes of administration, for instance such as rectal administration, are not excluded.

Suitable excipients are organic or inorganic substances which are suitable for enteral (e.g. oral), parenteral or topical administration and which do not react with a compound of formula I according to claim 1 such as (2R,4R)-2-({[5-(4-fluorophenyl)-pyridin-3ylmethyl]-amino}-methyl)-chroman-4-ol and/or one of its biocompatible salts or solvates, for example water, vegetable oils, benzyl alcohols, alkylene glycols, polyethylene glycols, glycerol triacetate, gelatine, carbohydrates such as lactose or starch, magnesium stearate, talc, petroleum jelly. Forms which are used for oral administration are, in particular, tablets, pills, sugar-coated tablets, capsules, powders, granules, syrups, liquids or drops, forms for rectal administration are, in particular, suppositories, forms for parenteral administration are, in particular, solvents, preferably oily or aqueous solutions, furthermore suspensions, emulsions or implants, and forms for topical administration are transdermal plasters, ointments, creams or powders. The compounds of formula I according to claim 1 and/or their pharmaceutically acceptable salts and solvates may also be lyophilized and the resulting lyophilisates used for example for the preparation of injectable products. The abovementioned preparations can be in sterilized form and/or comprise auxiliaries such as glidants, preservatives, stabilizers and/or wetting agents, emulsifiers, salts for modifying the osmotic pressure, buffer substances, colourings, flavourings and/or other active ingredients, e.g. one or more vitamins.

Preparations may, if desired, be designed to give slow release of (2R,4R)-2-({[5-(4-fluorophenyl)-pyridin-3ylmethyl]-amino}-methyl)-chroman-4-ol or a biocompatible salt or solvate thereof.

EXAMPLES

Example 1

(2R,4R/S)-2-({[5-(4-fluorophenyl)-pyridin-3ylmethyl]-amino}-methyl)-chroman-4-ol A stirred suspension of 3,5 g (2R,4R/S)-2-chloromethyl-4-hydroxy-chromane in 200 ml acetonitrile is treated with 4.5 g triethylamine to yield a yellow solution. To this solution 4 g sodium bicarbonate and 4 g 3-(4-fluorophenyl)-pyridyl-5-methylammonium hydrochloride in 100 ml acetonitrile is added. The reaction mixture is refluxed over night to yield a red solution. The mixture was evaporated, the resulting residue is taken up with ethyl acetate and washed with water and dried with sodium sulfate. The organic solution is evaporated to dryness. The resulting residue is purified by chromatography. The pure compound is converted to (2R,4R/S)-2-({[5-(4-fluorophenyl)-pyridin-3ylmethyl]-amino}-methyl)-chroman-4-ol hydrochloride in ethanol. Fp. 165 degrees C. The yield was 800 mg. Besides the N-monoalkylated compound, N-dialkylated and starting material is obtained.

Example 2

(2R/S)-2-({[5-(4-fluorophenyl)-pyridin-3ylmethyl]-amino}-methyl)-chroman-7-ol 1. 300 mg of (2R/S)-2-[5-(4-fluorophenyl)-3-pyridylmethylaminomethyl]-7-methoxychroman is treated with 25 ml hydrobromic acid (48% in water) at 130 degrees C. The obtained red solution is neutralized and worked up as described in example 1. 130 mg of (2R/S)-2-({[5-(4-fluorophenyl)-pyridin-3ylmethyl]-amino}-methyl)-chroman-7-ol hydrobromide is obtained;

RF=0.27 in ethyl acetate/methanol 8/2.

Similarly, 2-({[5-(4-fluoro-phenyl)-pyridin-3-ylmethyl]-amino}-methyl)-chroman-7-ol as maleate is obtained.

2. Analoguosly to example 2.1, (2R/S)-2-({[5-(4-fluorophenyl)-pyridin-3ylmethyl]-amino}-methyl)-8-methoxychroman is treated with hydrobromic acid to obtain (2R/S)-2-({[5-(4-fluorophenyl)-pyridin-3ylmethyl]-amino}-methyl)-chroman-8-ol hydrobromide.

Example 3

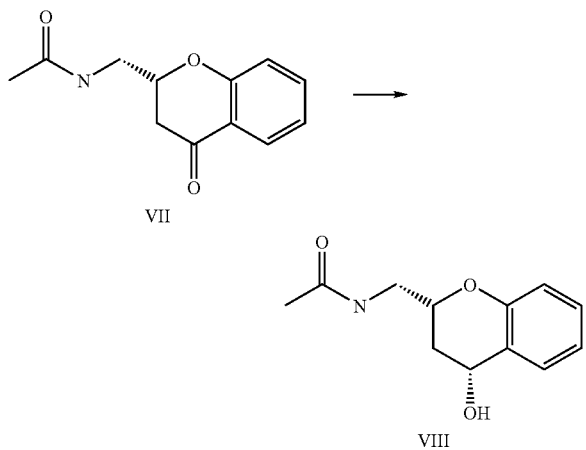

During 2 hours, a total of 26.0 g sodium borohydride was added in small portions to the stirred mixture of 20.0 g of a compound of formula VII in 250 ml of methanol. After stirring the mixture for one hour at room temperature, 500 ml of water and 800 ml of ethylacetate was added. The organic layer was separated, the solvent removed and the residue subjected to conventional work-up. After crystallization from toluene, the enatiomerically and diastereomerically pure compound of formula VIII was obtained.

Example 4

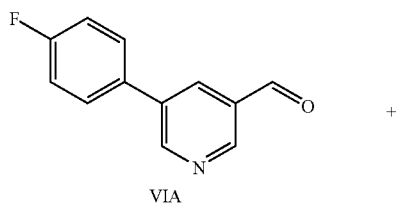

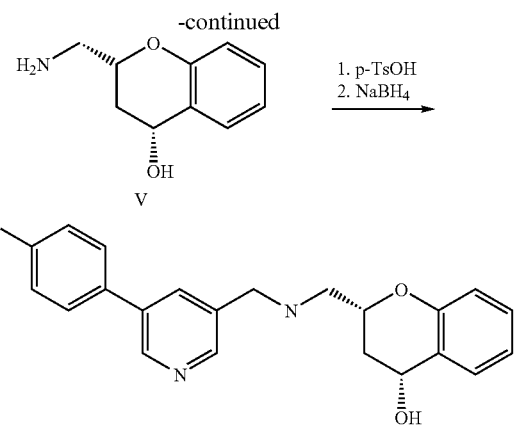

A solution of 3.7 g aldehyde VIA and 3.3 g amine V (obtainable according to WO 02/20507, Example 3 (2), from a compound of formula VIII) and a catalytic amount of p-toluenesulfonic acid in 280 ml toluene was refluxed for three hours using a water separator. The mixture was allowed to cool to room temperature prior to the addition of 100 ml methanol. During 30 minutes, a total of 4.0 g sodium borohydride was added in small portions to the stirred mixture. After stirring the mixture for one hour at room temperature, 100 ml of water and 200 ml of ethylacetate was added. The organic layer was separated, the solvent removed and the residue subjected to conventional work-up. Thereby, the free base (2R,4R)-2-({[5-(4-fluorophenyl)-pyridin-3ylmethyl]-amino}-methyl)-chroman-4-ol was obtained.

In order to prepare the corresponding hydrochloride, the product was dissolved in 100 ml ethanol and treated with 14,27 ml of a 1N solution of hydrochloric acid in water. The solvents were removed and the residue recrystallized from 50 ml of ethanol. Thereby, the compound (2R,4R)-2-({[5-(4-fluorophenyl)-pyridin-3ylmethyl]-amino}-methyl)-chroman-4-ol was obtained as monohydrochloride-hemihydrate in enantiomerically pure form.

Example 5

The affinity to the 5-$HT_{1A}$ receptor can be determined in vitro by radioligand binding experiments according to Cossery J M et al. (Eur. J. Pharmacol. 1987; 140: 143-155). The functional agonistic properties at the 5$HT_{1A}$ receptor can be determined in vitro in the GTP-gamma-S test (Newman-Tancredi A et al., Eur. J. Pharmacol.1996; 307: 107-111). A standard in vivo animal model to test for the 5$HT_{1A}$ agonistic properties is the ultrasonic vocalization test in rats (e.g. deFry J et al., Eur. J. Pharmacol. 1993; 249: 331-339; Sanchez C, Behav. Pharmacol. 1993; 4: 269-277). The affinity for dopamine D4 receptors can be determined in vitro by radioligand binding experiments according to Klokow M et al. (Drug Res. 1986; 36: 197-200). Compound (2R,4R)-2-({[5-(4-fluorophenyl)-pyridin-3ylmethyl]-amino}-methyl)-chroman-4-ol binds to 5$HT_{1A}$ receptors with an $IC_{50}$ value of 10 nM and to D4 receptors with an $IC_{50}$ of 12 nM. Furthermore, it has no or only a very weak binding to D2 receptors. Its 5$HT_{1A}$ agonistic properties are confirmed in vitro in the GTP-gamma-S test with an $ED_{50}$ of 33 nM and in vivo in the ultrasonic vocalization test with an $ED_{50}$ of 2 mg/kg.

The examples which follow relate to pharmaceutical products:

Example A

Vials

A solution of 100 g of (2R,4R)-2-({[5-(4-fluorophenyl)-pyridin-3ylmethyl]-amino}-methyl)-chroman-4-ol or a physiologically acceptable salt or solvate thereof and 5 g of disodium hydrogen phosphate in 3 l of twice-distilled water is brought to pH 6.5 with 2N hydrochloric acid, filter-sterilized, filled into vials, lyophilized under sterile conditions and sealed in sterile form. Each vial comprises 5 mg of active ingredient.

Example B

Suppositories

A mixture of 20 g of (2R,4R)-2-({[5-(4-fluorophenyl)-pyridin-3ylmethyl]-amino}-methyl)-chroman-4-ol or a physiologically acceptable salt or solvate thereof is melted with 100 g of soya lecithin and 1400 g of cocoa butter, and the mixture is poured into moulds and left to cool. Each suppository comprises 20 mg of active ingredient.

Example C

Solution

A solution is prepared from 1 g of (2R,4R)-2-({[5-(4-fluorophenyl)-pyridin-3ylmethyl]-amino}-methyl)-chroman-4-ol or a physiologically acceptable salt or solvate thereof, 9.38 g of $NaH_2PO_4.2H_2O$, 28.48 g of $Na_2HPO_4.12H_2O$ and 0.1 g of benzalkonium chloride in 940 ml of twice-distilled water. The pH is brought to 6.8, and the solution is made up to 1 l and sterilized by irradiation. This solution can be used in the form of eyedrops.

Example D

Ointment 500 mg of (2R,4R)-2-({[5-(4-fluorophenyl)-pyridin-3ylmethyl]-amino}-methyl)-chroman-4-ol or a physiologically acceptable salt or solvate thereof are mixed with 99.5 g of petroleum jelly under aseptic conditions.

Example E-1

Tablets

A mixture of 1 kg of (2R,4R)-2-({[5-(4-fluorophenyl)-pyridin-3ylmethyl]-amino}-methyl)-chroman-4-ol or a physiologically acceptable salt or solvate thereof, 4 kg of lactose, 1.2 kg of potato starch, 0.2 kg of talc and 0.1 kg of magnesium stearate is tableted in the customary manner in such a way that each tablet comprises 10 mg of active ingredient.

Example E-2

Tablets

A mixture of 20 g of (2R,4R)-2-({[5-(4-fluorophenyl)-pyridin-3ylmethyl]-amino}-methyl)-chroman-4-ol monohydrochloride hemihydrate, 1 kg of l-dopa, 250 g benserazide, 4 kg of lactose, 1.6 kg of potato starch, 0.2 kg of talc and 0.1 kg of magnesium stearate is tableted in the customary manner in such a way that each tablet comprises 0,2 mg (2R,4R)-2-({[5-(4-fluorophenyl)-pyridin-3ylmethyl]-amino}-methyl)-chroman-4-ol monohydrochloride hemihydrate, 10 mg of l-dopa and 2,5 mg benserazide.

Example F

Sugar-Coated Tablets

A mixture is tableted analogously to Example E, and the tablets are subsequently coated in the customary manner with a coating of sucrose, potato starch, talc, tragacanth and colouring.

Example G

Capsules 2 kg of (2R,4R)-2-({[5-(4-fluorophenyl)-pyridin-3ylmethyl]-amino}-methyl)-chroman-4-ol or a physiologically acceptable salt or solvate thereof are filled into hard gelatin capsules in the customary manner to that each capsule comprises 20 mg of the active ingredient.

Example H

Ampoules

A solution of 1 kg of (2R,4R)-2-({[5-(4-fluorophenyl)-pyridin-3ylmethyl]-amino}-methyl)-chroman-4-ol or a physiologically acceptable salt or solvate thereof in 60 l of twice-distilled water is filter-sterilized, filled into ampoules, lyophilized under sterile conditions and sealed in sterile form. Each ampoule comprises 10 mg of active ingredient.

Example I

Spray for Inhalation 14 g of (2R,4R)-2-({[5-(4-fluorophenyl)-pyridin-3ylmethyl]-amino}-methyl)-chroman-4-ol or a physiologically acceptable salt or solvate thereof are dissolved in 10 l of isotonic NaCl solution, and the solution is filled into commercially available pump-operated spray containers. The solution can be sprayed into mouth or nose. One actuation (approximately 0.1 ml) corresponds to a dose of approximately 0.14 mg.

The invention claimed is:

1. A pharmaceutical composition comprising a pharmaceutically acceptable salt of a compound of formula IA

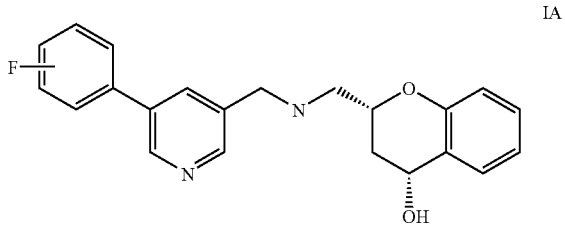

wherein said salt is formed from an acid selected from the group consisting of hydrochloric acid, hydrobromic acid, sulphuric acid, phosphoric acid, methanesulphonic acid, ethanesulphonic acid, toluenesulphonic acid, benzenesulphonic acid, naphthalene acid, disulphonic acid, acetic acid, propionic acid, lactic acid, tartaric acid, citric acid, fumaric acid, maleic acid and benzoic acid, including optical isomers thereof, and which
  A) is in the form of a tablet, pill, sugar-coated tablet, capsule, suppository transdermal plaster, ointment, cream or lyophilisate, and which comprises a solid, liquid or semiliquid excipient or adjunct; or
  B) 1) comprises a solid, liquid or semiliquid excipient or adjunct which is not water, or
    2) comprises a vegetable oil, benzyl alcohol, alkylene glycol, polyethylene glycol, glycerol triacetate, gelatine, carbohydrate lactose, starch, magnesium stearate, talc, or petroleum jelly.

2. A pharmaceutical composition according to claim 1, which contains a pharmaceutically acceptable salt of(2R, 4R)-2-({[5-(4-fluorophenyl)-pyridin 3ylmethyl]-amino}-methyl)-chroman-4-ol.

3. A pharmaceutical composition according to claim 1, further comprising at least one anti-Parkinsonian drug.

4. A pharmaceutical composition according to claim 3, wherein said anti-Parkinsonian drug is l-dopa.

5. A pharmaceutical composition according to claim 2, which contains the monohydrochloride hemihydrate of (2R, 4R)-2-({[5-(4-fluorophenyl)-pyridin-3ylmethyl]-amino}-methyl)-chroman-4-ol.

6. A pharmaceutical composition according to claim 1, which contains the monohydrochloride hemihydrate of(2R, 4R)-2-({[5-(4-fluorophenyl)-pyridin-3ylmethyl]-amino}-methyl)-chroman-4-ol.

7. A pharmaceutical composition according to claim 1, which comprises at least one solid, liquid or semiliquid excipient or adjunct, which is not water.

8. A pharmaceutical composition according to claim 2, which compromises at least one solid, liquid or semiliquid excipient or adjunct, which is not water.

9. A pharmaceutical composition comprising compound of formula IA

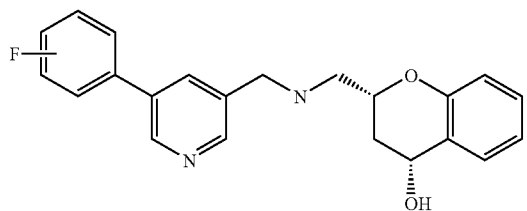

or a pharmaceutically acceptable salt of a compound of formula IA, including optical isomers thereof,
  wherein said pharmaceutically acceptable salt is formed from an acid selected from hydrochloric acid, hydrobromic acid, sulphuric acid, phosphoric acid, methanesulphonic acid, ethanesulphonic acid, toluene sulphonic acid, benzenesulphonic acid, naphthalene-disulphonic acid, acetic acid, propionic acid, lactic acid, tartaric acid, citric acid, fumaric acid, maleic acid, and benzoic acid, including optical isomers thereof, and which
    A) is in the form of a tablet, pill, sugar-coated tablet, capsule, suppository transdermal plaster, ointment, cream or lyophilisate, and which comprises a solid, liquid or semiliquid excipient or adjunct: or
    B) 1) comprises a solid, liquid or semiliquid excipient or adjunct which is not water, or
      2) comprises a vegetable oil, benzyl alcohol, alkylene glycol, polyethylene glycol, glycerol triacetate, gelatine, carbohydrate lactose, starch, magnesium stearate, talc, or petroleum jelly.

10. A pharmaceutical composition according to claim 9, which comprises (2R,4R)-2-({[5-(4fluorophenyl)-pyridin-3ylmethyl]-amino}-methyl)-chroman-4-ol, or a pharmaceutically acceptable salt of it.

11. A pharmaceutical composition according to claim 1, which is in the form of a tablet, pill, sugar-coated tablet, capsule, suppository, transdermal plaster, ointment, cream or lyophilisate, and which comprises a solid, liquid or semiliquid excipient or adjunct.

12. A pharmaceutical composition according to claim 2, which is in the form of a tablet, pill, sugar-coated tablet, capsule, suppository, transdermal plaster, ointment, cream or lyophilisate, and which comprises a solid, liquid or semiliquid excipient or adjunct.

13. A pharmaceutical composition according to claim 1, which comprises a vegetable oil, benzyl alcohol, alkylene glycol, polyethylene glycol, glycerol triacetate, gelatine, carbohydrate, lactose, starch, magnesium stearate, talc, or petroleum jelly.

14. A pharmaceutical composition according to claim 2, which comprises a vegetable oil, benzyl alcohol, alkylene glycol, polyethylene glycol, glycerol triacetate, gelatine, carbohydrate, lactose, starch, magnesium stearate, talc, or petroleum jelly.

15. A pharmaceutical composition according to claim 9, which comprises at least one solid, liquid or semiliquid excipient or adjunct, which is not water.

16. A pharmaceutical composition according to claim 10, which comprises at least one solid, liquid or semiliquid excipient or adjunct, which is not water.

17. A pharmaceutical composition according to claim 9, which is in the form of a tablet, pill, sugar-coated tablet, capsule, suppository, transdermal plaster, ointment, cream or lyophilisate, and which comprises a solid, liquid or semiliquid excipient or adjunct.

18. A pharmaceutical composition according to claim 10, which is in the form of a tablet, pill, sugar-coated tablet, capsule, suppository, transdermal plaster, ointment, cream or lyophilisate, and which comprises a solid, liquid or semiliquid excipient or adjunct.

19. A pharmaceutical composition according to claim 9, which comprises a vegetable oil, benzyl alcohol, alkylene glycol, polyethylene glycol, glycerol triacetate, gelatine, carbohydrate, lactose, starch, magnesium stearate, talc, or petroleum jelly.

20. A pharmaceutical composition according to claim 10, which comprises a vegetable oil, benzyl alcohol, alkylene glycol, polyethylene glycol, glycerol triacetate, gelatine, carbohydrate, lactose, starch, magnesium stearate, talc, or petroleum jelly.

* * * * *

UNITED STATES PATENT AND TRADEMARK OFFICE
CERTIFICATE OF CORRECTION

PATENT NO. : 7,618,988 B2  Page 1 of 1
APPLICATION NO. : 10/489960
DATED : November 17, 2009
INVENTOR(S) : Böttcher et al.

It is certified that error appears in the above-identified patent and that said Letters Patent is hereby corrected as shown below:

Column 27, line 3 claim 1 reads "phonic acid, naphthalene acid, disulphonic acid, acetic acid,", should read -- phonic acid, naphthalene-disulphonic acid, acetic acid, --.

Column 27, line 26 claim 5 reads "which contains the monohydrochloride hemihydrate of (2R,", should read -- which contains the monohydrochloride of (2R, --.

Column 27, line 37 claim 8 reads "which compromises at least one solid, liquid or semiliquid", should read -- which comprises at least one solid, liquid or semiliquid --.

Column 27, line 58 claim 9 reads "phonic acid, ethanesulphonic acid toluene sulphonic", should read -- phonic acid, ethanesulphonic acid toluenesulphonic --.

Column 28, line 12 claim 10 reads "which comprises (2R,4R)-2-({[5-(4fluorophenyl)-pyridin-", should read -- which comprises (2R,4R)-2-({[5-(4-fluorophenyl)-pyridin- --.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO.       : 7,618,988 B2
APPLICATION NO.  : 10/489960
DATED            : November 17, 2009
INVENTOR(S)      : Böttcher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1031 days.

Signed and Sealed this

Twenty-sixth Day of October, 2010

David J. Kappos
*Director of the United States Patent and Trademark Office*